(12) United States Patent
Ede et al.

(10) Patent No.: US 7,588,030 B2
(45) Date of Patent: Sep. 15, 2009

(54) MEDICAMENT CONTAINER AND METHOD OF MANUFACTURE THEREOF

(75) Inventors: Andrew John Ede, Cambridge (GB); John Kelshaw Conway, Cambridge (GB); Christopher Michael Wright, Cambridge (GB)

(73) Assignee: Meridica Limited, Melbourn Hertfordshire (GB)

( * ) Notice: Subject to any disclaimer, the term of this patent is extended or adjusted under 35 U.S.C. 154(b) by 1209 days.

(21) Appl. No.: 10/503,818

(22) PCT Filed: Feb. 6, 2003

(86) PCT No.: PCT/GB03/00536

§ 371 (c)(1), (2), (4) Date: Aug. 6, 2004

(87) PCT Pub. No.: WO03/066470

PCT Pub. Date: Aug. 14, 2003

(65) Prior Publication Data

US 2005/0084700 A1    Apr. 21, 2005

(30) Foreign Application Priority Data

Feb. 7, 2002    (GB) ................................. 0202911.4

(51) Int. Cl.
*A61M 15/00* (2006.01)
*A61M 16/00* (2006.01)

(52) U.S. Cl. ...................... 128/203.21; 128/203.12; 128/203.15; 53/453; 53/561; 264/524

(58) Field of Classification Search ............ 128/203.12, 128/203.15, 203.21; 53/456, 561; 264/524
See application file for complete search history.

(56) References Cited

U.S. PATENT DOCUMENTS

| 4,489,018 A | 12/1984 | Ball |
| 5,622,166 A | 4/1997 | Eisele et al. |
| 6,029,663 A | 2/2000 | Eisele et al. |
| 6,245,339 B1 | 6/2001 | Van Oort et al. |

FOREIGN PATENT DOCUMENTS

| DE | 836 170 | 4/1952 |
| DE | 195 25 615 A1 | 1/1997 |
| GB | 2 304 624 A | 3/1997 |
| WO | WO 01/17595 A1 | 3/2001 |

*Primary Examiner*—Patricia M Bianco
*Assistant Examiner*—Nihir Patel
(74) *Attorney, Agent, or Firm*—Foley & Lardner LLP

(57) ABSTRACT

A medicament container and a method of manufacturing the container housing at least one individual dose of medicament using a carrier having first and second opposing faces and through walls defining a through hole extending between the first and second opposing faces, the method including inserting the carrier into a mould having an element for protrusion into the through hole from the first face so as to define with the through walls a generally cup-shaped space, filling the generally cup-shaped space with a mould material so as to form a generally cup-shaped insert in the through hole, removing the carrier and insert from the mould, depositing an individual dose of medicament in the generally cup-shaped insert, and sealing the medicament and insert in the through hole by sealing first and second sheets respectively with the first and second faces.

14 Claims, 7 Drawing Sheets

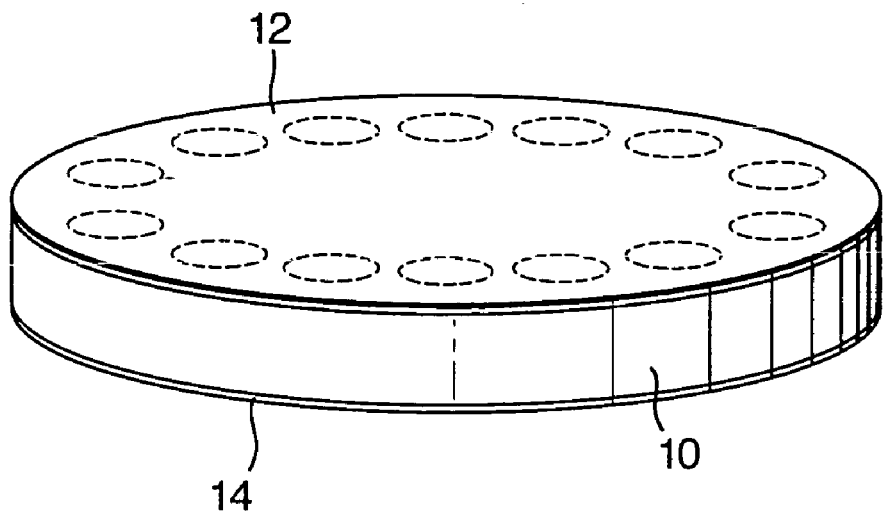
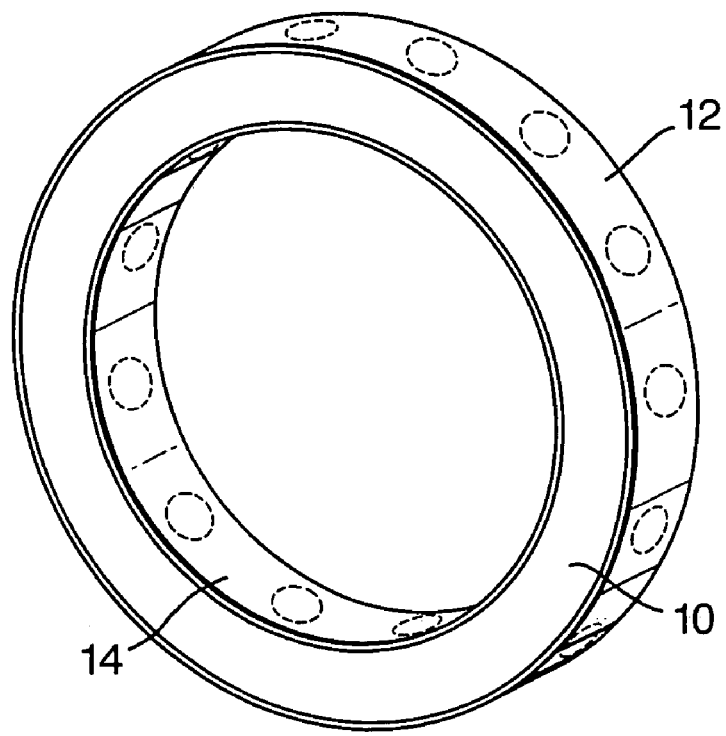

Fig.(7b)

MEDICAMENT CONTAINER AND METHOD OF MANUFACTURE THEREOF

The present invention relates to a medicament container and method of manufacture thereof, in particular to containers housing or for housing at least one individual dose of medicament and methods of manufacture thereof.

In the field of dry powder drug delivery, it is known to pre-meter individual unit doses of medicament into respective compartments of a pack, such that individual compartments may be opened and individual unit doses of medicament may be dispensed.

The compartments may be formed as so called blister packs in which preformed pockets or blisters are sealed with a lidding foil.

In order to open the compartments, the lidding foil may be pierced using a sharp edge to puncture the foil, so as to allow air to flow into and out of the compartments. In doing so, the foil is pressed into the compartment, thereby preventing the compartment from being fully opened, such that it is not fully or repeatably emptied of the powder.

It is also possible to peel the foil away from the base so as to open the compartments. However, the dispensing devices used to do this are more complex, since it is necessary to control the tension of the lidding foil and to control accurately the amount of unpeel such that only one compartment is opened at a time. Additionally, the compartments must be spaced out so as to simplify the positional control. This increases the size of the blister pack and the dispensing device.

The present invention contemplates the use of generally cup-shaped inserts within respective pockets of the blister pack. Each cup-shaped insert contains a unit dose of medicament and may be pushed from the underside of the blister pack so as to burst the lidding sheet outwardly of the blister pack and expose the medicament for dispensing.

Thus, a member, separate from the base and the lidding sheet, is provided to rupture the lidding sheet outwardly. In this way, it is not necessary to provide a complex unpeeling mechanism and the compartments of the pack may be spaced closely with respect to one another. Furthermore, the lidding sheet may be opened outwardly of the recesses such that the recesses become fully opened to air flow and allow complete removal of powder from the compartments. By providing the insert as a rigid member within the compartment to rupture the lidding sheet, pressure from the underside to cause rupturing of the lidding sheet does not compress or agglomerate the medicament within the pack. This is clearly of significant advantage when the medicament is a dry powder form, for instance for inhalation into the lungs or the nasal cavities.

Unfortunately, providing the inserts in the individual pockets of the blister pack increases the complexity and cost of manufacture. Furthermore, there are inherent design restrictions with use of a conventional blister pack where the pockets are formed by deep drawing a film or sheet.

It is an object of the present invention to provide a medicament container and a method of manufacture thereof which makes use of the advantages discussed above whilst reducing the complexity and cost of manufacture.

According to the present invention, there is provided a method of manufacturing a container for housing at least one individual dose of medicament using a carrier having first and second opposing faces and through walls defining a through hole extending between the first and second opposing faces, the method including:

inserting the carrier into a mould having an element for protrusion into the through hole from the first face so as to define with the through walls a generally cup-shaped space;

filling the generally cup-shaped space with a moulding material so as to form a generally cup-shaped insert in the through hole; and removing the carrier and insert from the mould whereby an individual dose of medicament may be deposited in the generally cup-shaped insert and the medicament and insert sealed in the through hole by means of first and second sheets sealed respectively with the first and second faces.

According to the present invention, there is also provided a container for housing at least one individual dose of medicament, the container including:

a carrier having first and second opposing faces and through walls defining a through hole extending between the first and second opposing faces; and a generally cup-shaped insert formed in the through hole by inserting the carrier into a mould having an element for protrusion into the through hole from the first face so as to define with the through walls a generally cup-shaped space and filling the generally cup-shaped space with a moulding material so as to form the generally cup-shaped insert in the through hole whereby an individual dose may be deposited in the generally cup-shaped insert and the medicament and insert sealed in the through hole by means of first and second sheets sealed respectively with the first and second faces.

This provides a container which may be filled with medicament according to the needs of medicament supplier.

In this respect, according to the present invention, there is also provided a method of providing at least one individual dose of medicament in a container using a carrier having first and second opposing faces and through walls defining a through hole extending between the first and second opposing faces and a generally cup-shaped insert formed in the through hole by inserting the carrier into a mould having an element for protrusion into the through hole from the first face so as to define with the through walls a generally cup-shaped space and filling the generally cup-shaped space with a moulding material so as to form the generally cup-shaped insert in the through hole, the method including:

depositing an individual dose of medicament in the generally cup-shaped insert; and sealing the medicament and insert in the through hole by sealing a first sheet with the first face, a second sheet being sealed with the second face.

The second sheet can be sealed to the second face as part of the method or the container can be provided with the second sheet already sealed to the second face such that it is only necessary to perform the steps of depositing the individual dose and sealing the first sheet.

According to the present invention there is also provided a method of manufacturing a container housing at least one individual dose of medicament using a carrier having first and second opposing faces and through walls defining a through hole extending between the first and second opposing faces, the method including:

inserting the carrier into a mould having an element for protrusion into the through hole from the first face so as to define with the through walls a generally cup-shaped space;

filling the generally cup-shaped space with a moulding material so as to form a generally cup-shaped insert in the through hole;

removing the carrier and insert from the mould;
depositing an individual dose of medicament in the generally cup-shaped insert; and
sealing the medicament and insert in the through hole by sealing first and second sheets respectively with the first and second faces.

According to the present invention there is also provided a container housing at least one individual dose of medicament, the container including:

a carrier having first and second opposing faces and through walls defining a through hole extending between the first and second opposing faces;

a generally cup-shaped insert formed in the through hole by inserting the carrier into a mould having an element for protrusion into the through hole from the first face so as to define with the through hole a generally cup-shaped space and filling the generally cup-shaped space with a moulding material so as to form the generally cup-shaped insert in the through hole;

an individual dose of medicament in the generally cup-shaped insert; and first and second sheets sealed respectively with the first and second faces.

It will be appreciated that containers including a plurality of through holes and inserts may be manufactured in exactly the same way so as to provide a plurality of individual doses of medicament.

In this way, the insert(s) may be formed and positioned in the container in the same manufacturing step. A medicament container is provided having the advantages discussed above for packs having outwardly bursting inserts and combining this with not only reduced cost and complexity but also improved tolerances and reliability. In particular, the tolerance of the volume of the cup-shaped space may be more precise than previous medicament holding space volumes.

It is also possible to provide pockets with depth to width ratios much higher than the conventional maximum for deep drawn blister packaging of approximately 2:5. This allows much larger numbers of doses to be contained for a given surface area.

Furthermore, it is possible to produce an insert in each through hole having a required shape and size such that the insert is a close enough fit to the through walls to prevent medicament passing therebetween and yet not so tight as to prevent movement of the insert when pushed. The protruding element allows the size and shape of the insert cavity to be easily chosen and changed.

The method may further include the step of forming the carrier with the through hole. The carrier may be formed by one of injection moulding, die casting, pressing, extrusion, casting, sintering, stamping, punching and coining and may be formed from one of polymers, metals, ceramics and composites.

The carrier should form a barrier to moisture and, hence, be completely impermeable. This may be achieved by forming the carrier from a metalised plastics material or aluminium.

Aluminium is a relatively cheap light material which may be formed easily into any appropriate shape with the required through holes.

The insert may be formed from a thermoplastic or thermosetting polymer, resin or any other material that can be injected as a fluid and then converted to a solid when in situ. For instance, the insert may be formed from one of a polymer, elastomer and monomer.

This allows the insert to be moulded easily within the through hole of the carrier.

Preferably, the first and second sheets are formed from aluminium. They may be aluminium composites or laminates and provide good moisture resistance and may easily be hermetically sealed to the carrier, particularly when this is also aluminium.

Preferably, the shape and size of the element is chosen to define the volume and shape of the space defined within the insert.

In this way, the form of the mould is able to define features of the internal surface of the insert, including volume, shape, etc. This allows the insert cavity to be moulded with a precise volume, thus enabling the cavity volume to be used for the metering of powder or fluid which is to be contained. Furthermore, the volume of the insert cavity can easily be changed by changing a single tooling component, i.e. the element, of the mould. The cup-shaped insert, by surrounding the housed medicament, also provides thermal insulation to the medicament during heat sealing of a first sheet to the first face.

Preferably, the fit of the insert in the through hole is controlled by controlling at least one of the injection pressure, the injection temperature, the surface finish of the through walls and a draught angle of the through walls.

This allows the insert to be fitted in the through hole such that medicament cannot pass between the insert and the through walls but allowing the insert to be pushed along its axis out of the through hole. Furthermore, the insert may be held in place in the through hole by its contact with the through walls without preventing the insert from being pushed out of the through hole.

Preferably, the adhesion of the insert in the through hole is controlled by controlling at least one of the preheat temperature of the carrier, the material of the insert and the fit of the insert, for instance as described above. The surface finish of the through walls will affect the insert's resistance to movement. Indeed, the through walls may be formed with specific features, such as protrusions or indents, around which the insert must deflect when being pushed axially out of the through hole.

Preferably, the generally cup-shaped space is filled with the moulding material from the second face.

Alternatively, the cup-shaped space can be filled with moulding material from the first face, for instance through a filling passage in the protruding element. In this way, the second sheet can already be sealed to the second face before moulding of the insert. Alternatively, the second sheet could be placed in the mould with the carrier and sealed to the carrier during the step of moulding the insert.

Thus, the insert may be filled in situ in the carrier.

Preferably, the mould at the second face is generally flush and co-planar with the second face. Thus, the closed end of the cup-shaped insert is generally flush and co-planar with the second face.

Although it is preferred that the wall of the insert ends in close proximity to the top edge of the through-hole, the mould could extend up into the through hole from the second face so that the insert is recessed behind the second face. However, construction of the mould and the processing is made more straightforward when the mould is co-planar with the second face. Furthermore, this results in the closed end of the insert being immediately accessible for pushing the insert out through the first face. In this respect, the mould could alternatively be formed such that the closed end of the insert protrudes beyond the second face.

Preferably, the insert fills the space of the through hole. This is a result of the process of moulding the insert in situ and ensures that the insert fits well in the through hole, is guided properly when moved to burst the first sheet and wastes no space. In particular, the insert fills completely a space between the through walls so as effectively, as far as particles of medicament are concerned, to seal the through hole. In other words, the periphery of the insert fits with the through walls to prevent particles, typically for example drug particles of the order of one micron for use in a dry powder inhaler, passing therebetween.

Preferably, the medicament is in dry powder form, suitable for inhalation to the nasal cavities or lungs.

Containers of the present invention are particularly suitable for such use.

According to the present invention, there is also provided a method of manufacturing a carrier including punching out the through holes. Preferred techniques for this are described below.

The invention will be more clearly understood from the following description, given by way of example only, with reference to the accompanying drawings, in which:

FIGS. 1(a) to (e) illustrate containers constructed according to the present invention;

Figure 7A:
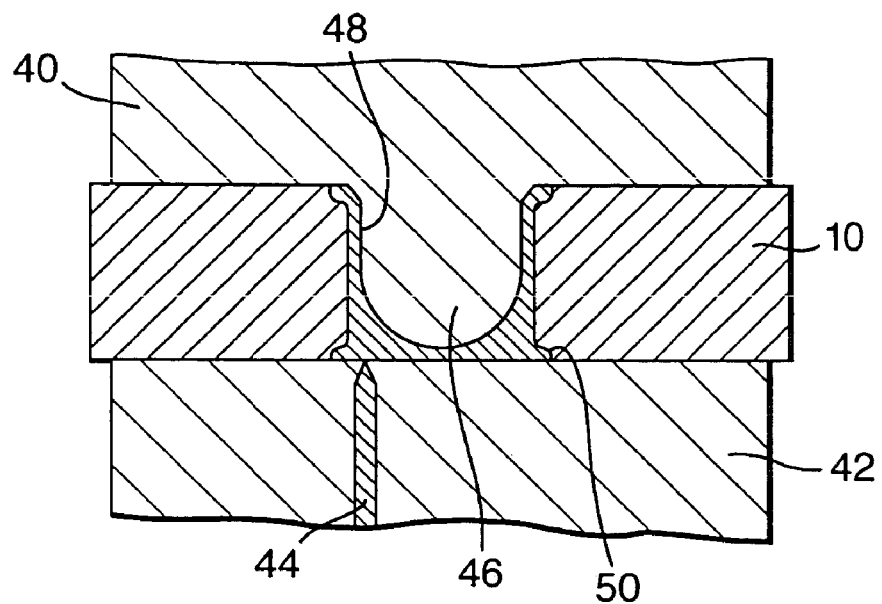
Figure 7A:
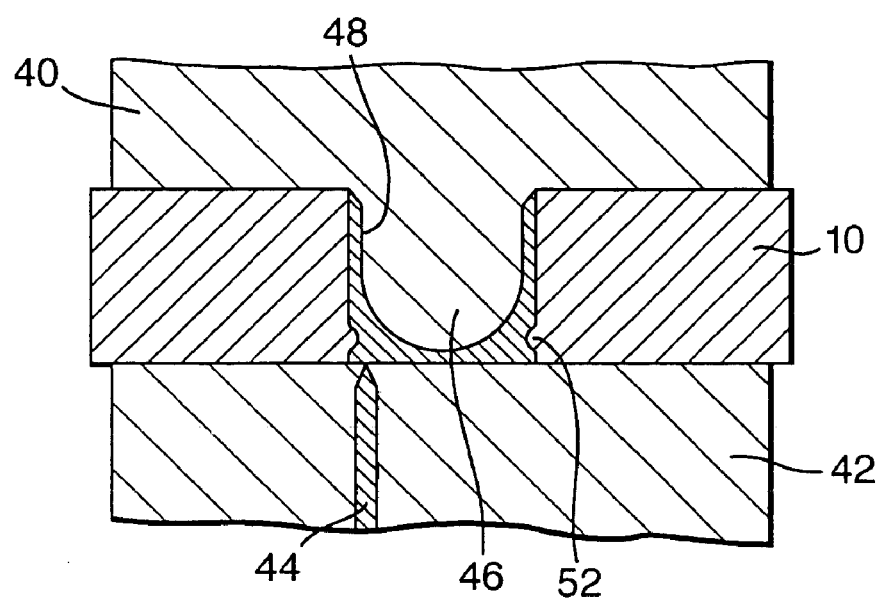

FIGS. 7(a) and (b) illustrate carriers with shaped through walls.

Figure 2:
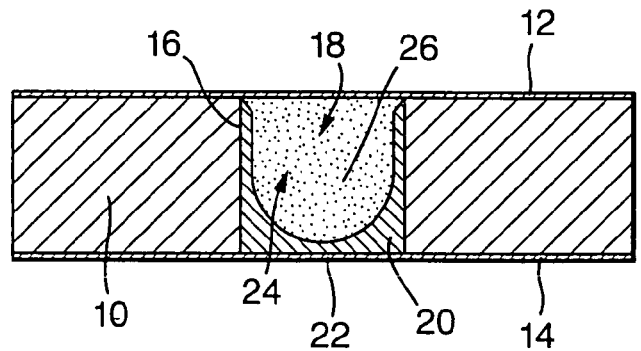
FIG. 2 illustrates a cross section of a pocket constructed according to the present invention.
Figure 8:
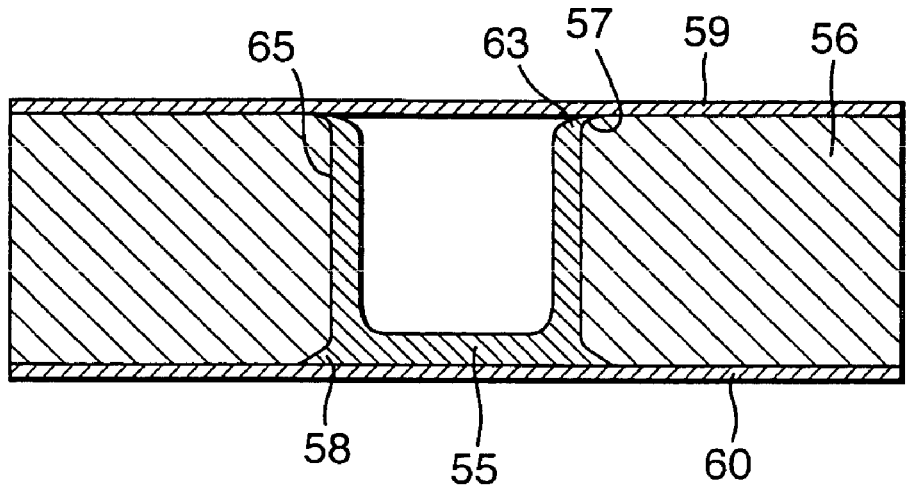
Figure 9:
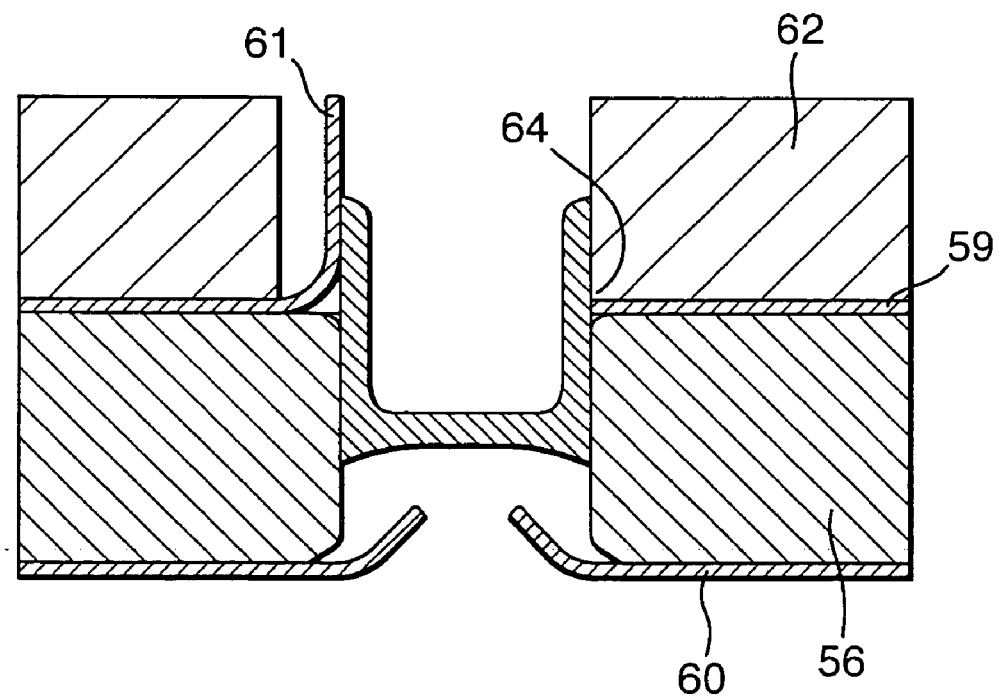
Figure 10A:
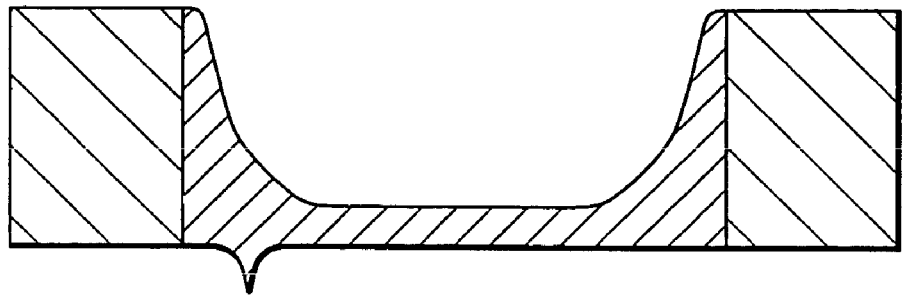
Figure 10B:
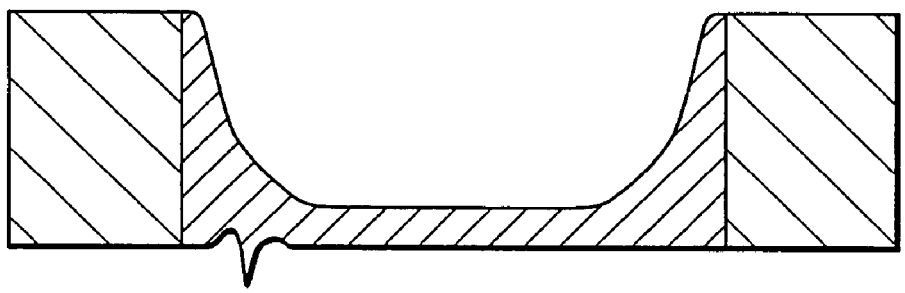
Figure 10C:

FIG. 8 illustrates in greater detail various tolerance features of a pocket similar to that of FIG. 2;

FIG. 9 illustrates the insert of FIG. 8 being pushed out of its through hole into a supporting anvil plate; and FIGS. 10(a) to (c) illustrate flashing produced during moulding.

Containers constructed according to the present invention may take a number of different forms. In particular, they may include one or a plurality of pockets for respective doses of medicament. These pockets may be arranged in arrays of any desired pattern and may be formed in carriers of any desired shape.

FIGS. 1(a) to (e) illustrate various examples.

Figure 1A:
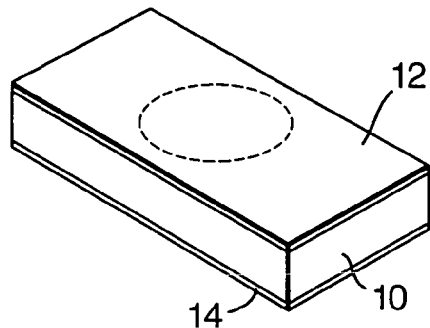
Figure 1B:
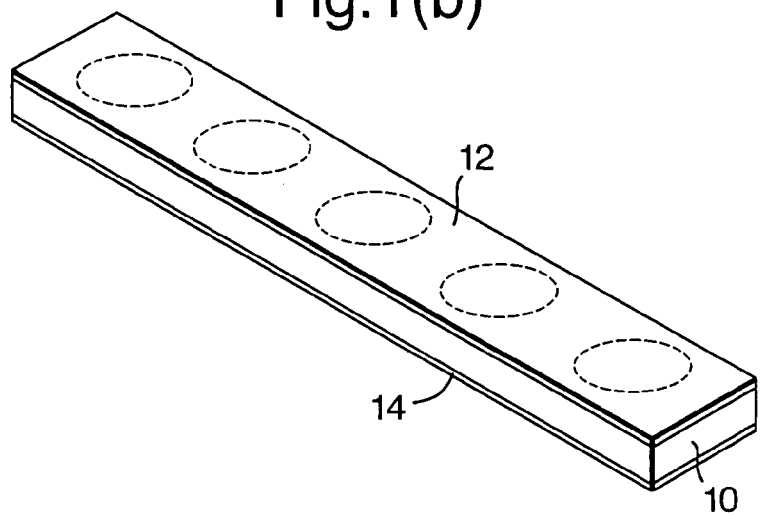
Figure 1C:
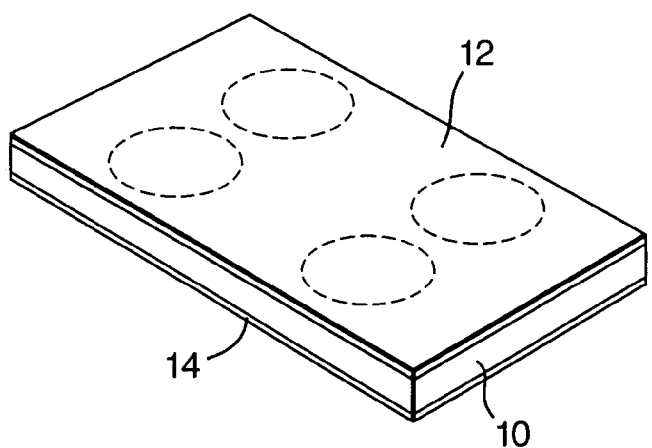

In all cases, a carrier 10 is provided with a lidding sheet 12 on a first face and a lidding sheet 14 on a second face. The sheets 12 and 14 seal one or more through holes in the carrier 10. Once sealed with the sheets 12 and 14, the through holes will not be visible. However, to aid in an understanding of the construction, the through holes are signified in the figures by dashed lines. Thus, it will be seen that the container of FIG. 1(a) includes a single pocket, the container of FIG. 1(b) has a strip-like or tape-like form with an elongate array of pockets, the container of FIG. 1(c) is planar with a two-dimensional array of pockets, the container of FIG. 1(d) is disk-shaped with a circumferential array of pockets and the container of FIG. 1(e) is drum shaped with a peripheral array of pockets.

FIG. 2 illustrates a cross section through a carrier showing one pocket. Through-walls 16 in the carrier 10 define a through hole 18. Formed within the through hole 18 is a generally cup-shaped insert 20. As illustrated, the outer volume of the cup-shaped insert 20 generally fills the through hole 18. Indeed, the closed end 22 of the insert 20 is generally co-planar and flush with the second face of the carrier 10.

As illustrated, the generally cup-shaped insert 20 has a recessed inner volume 24 forming a space in which to house a medicament, such as a powder 26. The open end 28 of the insert 20 forms a generally peripheral wall adjacent the lidding sheet 12.

Figure 3:
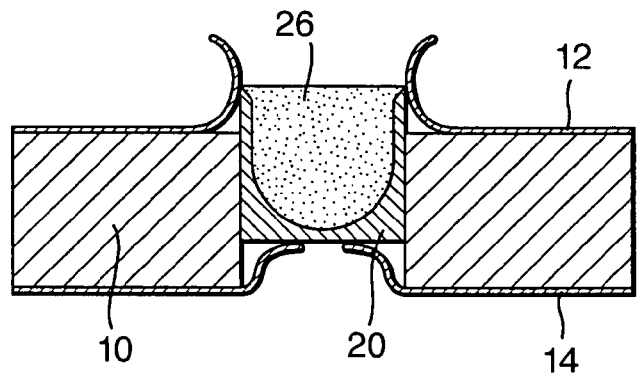
FIG. 3 illustrates the pocket of FIG. 2 with the insert pressed through a face.

As illustrated in FIG. 3, in use, pressure is applied to the closed end 22 of the insert 20 from the second face of the carrier 10 through the sheet 14. In this way, the insert 20 is moved upwardly out of the through hole 18 such that the walls of the open end 28 rupture the sheet 12. In this way, access is given to the medicament within the space 24 of the insert 20 such that it may be dispensed as required.

Figure 4:
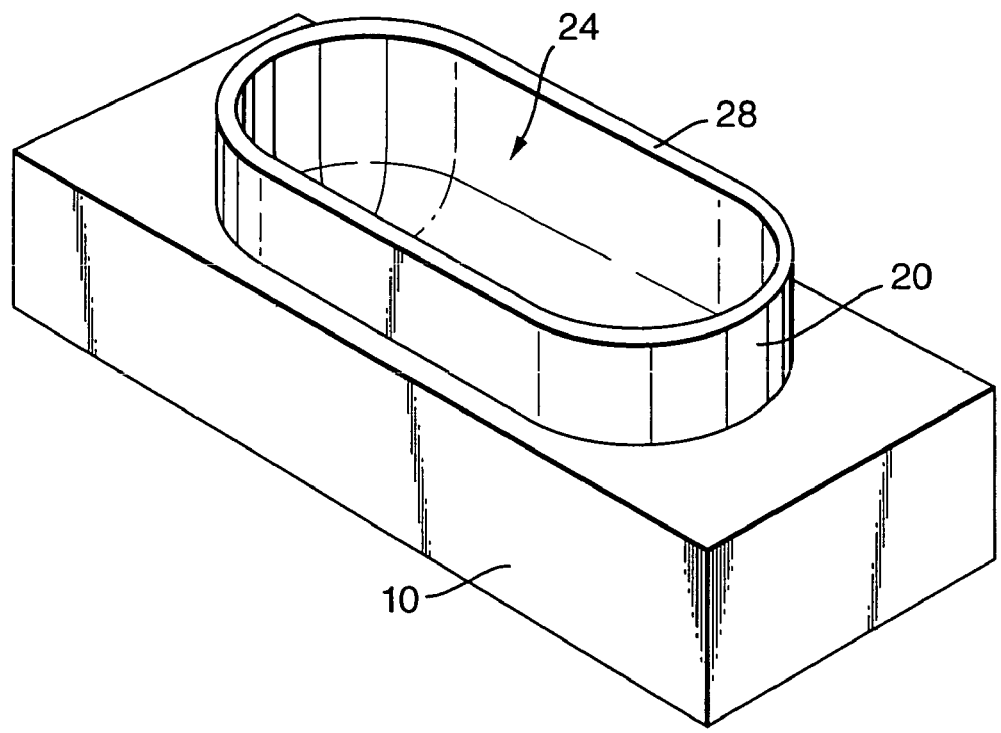
FIG. 4 illustrates a carrier with a protruding insert constructed according to the present invention.

FIG. 4 illustrates an insert 20 protruding from the first face of a carrier 10. For simplicity, this is illustrated without the sheets 12 and 14.

As will be appreciated from the following description, the construction of the insert 20 in the through hole 18 is particularly advantageous with regard to its method of manufacture. In particular, the insert 20 is moulded in situ in the carrier 10.

Figure 5:
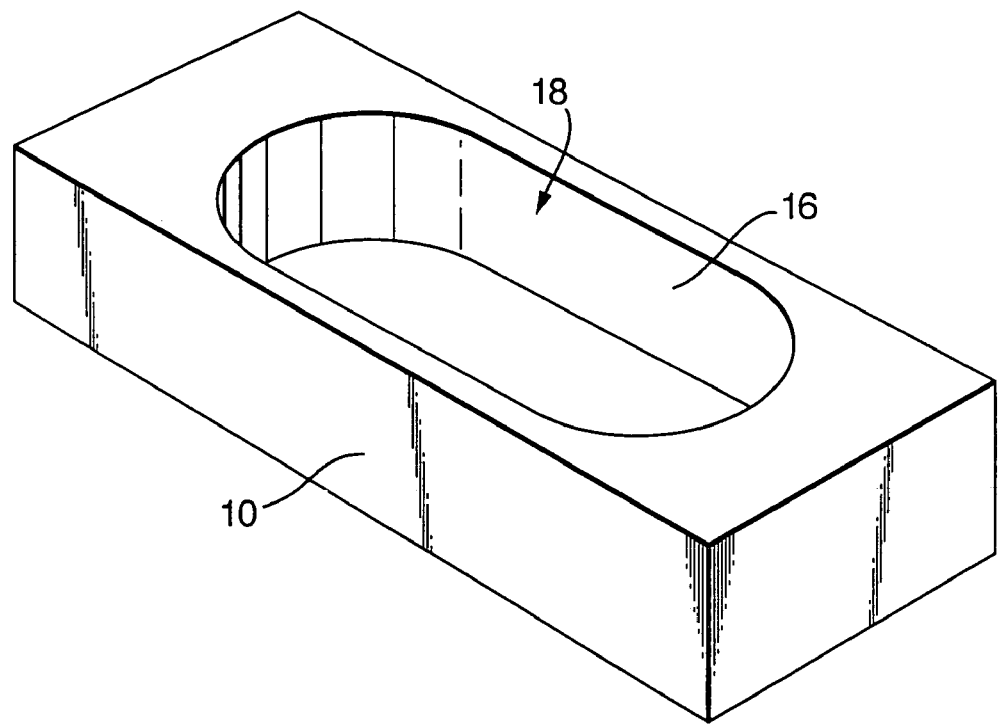
FIG. 5 illustrates a carrier for use with the present invention.

First, a carrier 10 is provided having one or more through holes 18. FIG. 5 illustrates for simplicity a carrier 10 having only one through hole. However, it will be appreciated that other carriers, for instance those illustrated in FIGS. 1(a) to (e) can also be provided. The carrier 10 may be manufactured from any suitable material, such as polymers, metals, ceramics, composites, etc. The choice of material will depend on the required moisture resistance properties, flexibility, weight, cost, etc. Since, as will be described below, the carrier 10 is also to be provided within a mould such that the insert 20 is moulded in situ, it is also important that the material of the carrier 10 be chosen to allow this process to be conducted.

In a preferred embodiment, the carrier 10 is constructed from a low water permeability plastic or composite plastic or aluminium.

The carrier 10 may be manufactured by any appropriate process, such as injection moulding, die casting, pressing, extrusion, casting, sintering, stamping, punching or coining. In particular, depending on the material chosen for the carrier 10, a process may be chosen which is capable of forming through holes 18 suitable for accepting the inserts 20.

The carrier 10 may be formed with through holes of any desired shape and not necessarily circular as illustrated in the figures. Indeed, for the embodiment of FIG. 1(d), it is preferred that the holes are elongate in a radial direction. For moisture resistance, there will be a minimum spacing between adjacent holes, but more efficient packing is obtained if the circumferential extent of the holes is reduced and the radial extent increased.

It is required that the insert 20 be able to slide along its axis within the through hole 16 and out of the first face. However, otherwise, the shape of the through hole 16 may be designed freely and the process for manufacturing the carrier 10 chosen accordingly.

The insert 20 is formed from a moulding process, preferably an injection moulding process.

Figure 6:
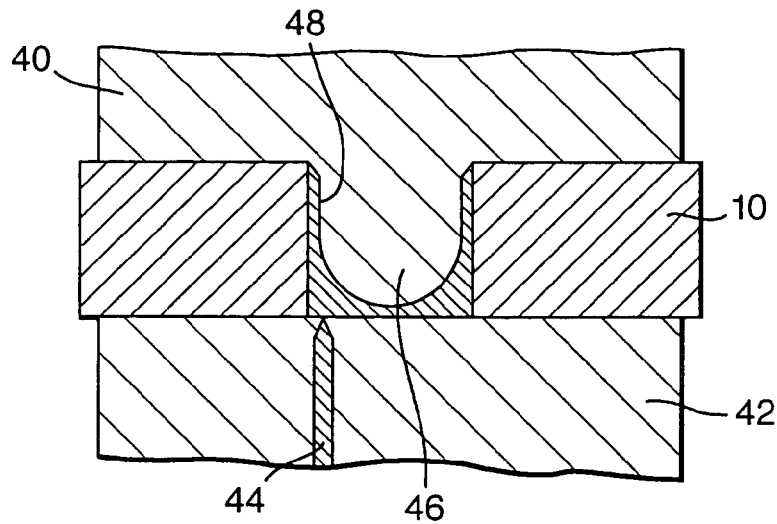
FIG. 6 illustrates the process of moulding an insert with a carrier according to the present invention.

The carrier 10 is inserted into a mould for forming the insert 20. As illustrated in FIG. 6, the carrier 10 is located between a first mould tool 40 and a second mould tool 42. The first mould tool 40 generally seals with the first face of the carrier 10 and the second mould tool 42 generally seals with the second face of the carrier 10. In this way, a moulding cavity is formed within the through hole 18.

A feed channel 44 is formed in the second mould tool 42. This allows moulding material to be injected into the cavity formed by the through hole 18.

As illustrated, the first mould tool 40 is formed with a protruding element 46 which extends from the first face of the carrier 10 into the through hole 18. An outer surface 48 of the protruding element 46 defines the inner surface of the insert 20 to be formed by the mould. On the other hand, the through walls 16 define the outer peripheral walls of the insert 20 and the face of the mould tool 42 defines the closed end of the insert 20. As illustrated, the resulting insert is formed with the cup-shaped space 24 for housing medicament and outer peripheral walls 28 for rupturing the first sheet.

It should be appreciated that, by this method, the fit of the insert 20 in the carrier 10 is independent of the shape and size of the insert cavity 24 formed by the protruding element 46. Similarly, the insert cavity 24 may be designed freely and is independent of the fit of the insert 20 in the carrier 10.

The carrier is placed into the tooling of an injection mould such that the carrier itself forms part of the mould cavity. The form of the mould tool, in particular the protruding element 46 is able to define features of the internal surface of the insert 20 including volume, shape, etc. This allows the insert cavity 24 to be created with a precise volume. This is particularly advantageous when the cavity volume is used to meter the required amount of medicament, for instance powder or fluid, which is to be contained. In particular, the insert cavity 24 may be completely filled with medicament, such that the volume of the insert cavity 24 is chosen to be the volume required for a single dose of medicament.

It will also be appreciated that, using this method of manufacture, the volume of the insert cavity 24 may be easily changed by changing a small part of the moulding tool, i.e. the protruding element 46. Indeed, it becomes easy to provide a variety of different insert cavity volumes, even within the same container.

As will be discussed in further detail below, the fit of the insert 20 in the carrier 10 is controlled by altering a number of parameters including the injection pressure and temperature, the surface finish of the internal surface, i.e. the through walls 16, of the through hole 18 or the draught angle on the through hole 18. Furthermore, the through walls can be formed with specific features, such as recesses 50 or protrusions 52, as illustrated in FIGS. 7(a) and (b), to resist movement of the insert.

In order to achieve good performance for specific embodiments of the concept, it is thus desirable to consider the requirements for the form of the holes in the carrier plate.

For the embodiment illustrated in FIGS. 2 and 3 where the insert 20 is to be pushed through the foil 12 on the first face such that it ruptures the foil cleanly, the requirements for the hole in the carrier plate will be described with respect to FIG. 8 and FIG. 9 where FIG. 8 shows the special requirements of the holes and FIG. 9 shows the insert being pushed up into an anvil plate 62 which controls the breaking of the foil. The anvil plate 62 supports and holds the foil on the top surface so as to provide a controlled rupturing of the foil.

The peripheral radius 57 of the through hole of the carrier plate 56 at the top surface, through which the insert 55 is to be pushed, may have an effect on the ultimate performance and usability of the container. If the radius is too small and the corner too sharp, it could tear the foil 59 when it is pressed down to seal it to the carrier 56. However, if the radius is too large and the corner too round, the top of the insert 63 will be formed into a peripheral lip which will catch on the corner 64 of the anvil plate 62 preventing the insert from moving up.

Preferably the radius 57 should be more than 0.025 mm and less than 0.10 mm for an insert wall thickness of 0.3 mm (not exceeding 30% of the wall thickness).

The peripheral radius 58 of the through hole at the bottom surface from which the insert is to be pushed may also have an effect on the performance and usability of the container. If the radius is too small and the corner too sharp, then it may damage the foil 60 on sealing. However, if the radius is too large and the corner too round, the base of the insert wall will form a peripheral lip extending wider than the width of the hole and the force needed to push the insert up becomes too large.

Preferably, the radius 58 falls within the same range as that described above for radius 57. Indeed, the radius 58 may be substantially the same as that for radius 57.

Typically, manufacturing methods for the holes in the carrier plate 56 can leave burrs, i.e. sharp bits of material, on the corners 57 and 58. In particular, where the holes are machined, top and bottom corners 57, 58 can have burrs and, where the holes are pierced, punched, broached or pressed, then there will be a rounding of the entry and burrs on the exit side.

Burrs that extend beyond the top or bottom surfaces are disadvantageous, since they can puncture the foil 59 or 60.

Burrs that extend into the hole can become trapped in the insert 55 during the moulding process and prevent the insert moving when it is pushed. Thus, preferably the overall manufacturing process includes the removal or reduction of any burrs caused in the manufacture of the through holes. In particular, any burrs extending beyond the top and bottom surfaces should be reduced to less than 25 microns (preferably less than 5 microns) and any burrs extending into the through holes should be reduced to less than 100 microns (preferably less than 50 microns).

The roughness of the inner wall 65 of the through hole also has an effect on the fit of the insert 55 in the carrier 56. If the wall 55 is too rough, then the frictional resistance to movement of the insert wall will be too high. On the other hand, if the wall 65 is too smooth, the inserts may fall out.

The method of manufacture of the hole will influence the form of the roughness on the pocket walls. Machining will produce grooves in the plane of the corner and punching/blanking will produce grooves orthogonal to the carrier plane.

Punched holes are preferred since they can provide the best finish. The grooves across the plate provide some friction but allow smooth movement to push out the insert.

Roughness in the range of 0.03 to 0.3 of the wall thickness of the insert is preferred.

Care may be required when punching holes to avoid the material tearing towards the exit face. This can produce a ridge around the hole that can produce excessive resistance to the insert motion.

The following description relates to the preferred manufacturing process of punching an aluminium sheet. For example, a carrier of the form shown in FIG. 1(d) may be provided as a disc with a circular array of holes with substantially parallel sides right though the disc.

This form of carrier could be made by machining the holes with drilling or milling operations. Conventional milling using an automated milling system (CNC) is possible but can be relatively expensive. Drilling could be used relatively cost effectively for circular holes, but not for other shapes. A custom machining tool using multiple milling heads could be cost effective for some hole shapes.

The present application recognises that, where the material and thickness of the plate allow, holes could be punched through the material. Aluminium is a material in which holes may be punched for thicknesses up to 5 mm. This approach allows the punching of any number of holes simultaneously with the appropriate tool design. This is therefore a highly advantageous and cost effective method of range 1 sec to 10 sec.

Punching a hole in a thick plate can produce a hole where the material surrounding the hole is deformed. In particular, there may be rounding of the entry edges, tearing of the material along the walls of the hole, burrs on the exit edge and/or depressions in the surfaces surrounding the hole.

The present application proposes a refinement to the punching process to achieve high quality for hole required to accommodate the inserts. Several approaches may be used, the choice depending specifically on the materials and dimensions required.

One approach is to use what might be termed fine blanking and to provide the material to be punched with close toleranced clamping all around the hole and to use a press and tooling that ensures precise control of the gaps between the punch tool and the surrounding clamps. With this level of accuracy, it is possible to reduce the rounding and tearing when using aluminium sheet material up to 3 mm thick.

Where deeper holes are required, then broaching may be necessary to achieve the required tolerance control. An initial hole is punched and then this is progressively widened by a series of cutters each just a little larger than the previous one.

Whatever punching approach is used, it is preferred to ensure that no sharp burrs remain at the exit corners. A finishing process is therefore preferred to ensure no burrs remain.

This may use: tumbling with grit, stones or balls; sand or grit blasting; electro etching/de-burring; and/or chemical de-burring. The technique selected will depend upon the requirement for the surface finish on the walls and surfaces for the carrier plate. For example, tumbling with grit may roughen all surfaces or produce random scratches on the surfaces. Where foil is to be sealing to the surface to provide a barrier, then any scratches deeper than the bonding later between the foil and surface would degrade the integrity of the seal. Alternatively, a finishing process that gives a very smooth surface might not provide sufficient friction for good adhesion of foil or to retain the inserts in place before foiling.

It is also possible to punch a sheet of plastics material. The manufacturing process required for punching plastics material to the required tolerance is different to that required for a metal. Taking for example 3 mm HDPE material to be punched for the carrier described in FIG. 1(d), punching can leave strings of material around the exit hole. This is because HDPE is a much softer material than aluminium and the pressure wave that is produced ahead of the cutting tool can cause material to extrude through the gaps between the press tool and the support plate.

Thus, to use punching with a plastics material, different tools and conditions will be required for each material and hole size.

The present application considers the following approaches: cooling the plastic to increase its stiffness sufficiently to enable simple punching work; broaching coring; punching of a core followed by a finishing operation using a shaped knife blade to shave a thin layer off the walls; and/or a heated knife blade to locally melt the plastic at the cutting edge.

For the case of producing round ended elongated holes of 2.5 mm width and 8.0 mm length in 3 mm thick HDPE, a two stage process is preferred. Initially, a rounded ended hole 1.9 mm wide 7.4 mm long is punched. This is followed by removing the remaining 0.3 mm of wall using a blade formed in the desired hole shape. To prevent stringing at the exit hole, the 3 mm HDPE sheet is clamped between rigid plates with an additional sheet of plastic material on the exit face. The blade is driven through the HDPE sheet to penetrate into the plastic sheet underneath.

Typically, the sheet thickness is between 0.25 mm and 1.0 mm and the blade penetrates a minimum of 0.2 mm into it.

The cutting edge of the blade is preferably angled on the hole side and plane on the outside. The centre of the cutting blade is preferably hollow to allow space for the cut material to occupy during the cutting process without it generating a lateral force on the blade. This swarf can be ejected after the cut.

Apart from punching, it is also possible to mould a plastics material carrier.

Taking the example of FIG. 1(d), it is possible to injection mould the carrier plate as an alternative to punching it as described above. There are advantages in simplifying the foil sealing process if the surfaces to which the foil will be sealed are flat. It is therefore desired that, for the moulding of such plates, the moulding process minimises any ejector pin marks, sink marks or gate flashing that prevent these surfaces being flat. For the example described, it is preferred to have a flatness of 50 microns or less, with 10 microns further preferred.

To achieve this, the moulding conditions should be optimised for the particular tool being used and large area ejector surfaces and distributed gating should be used to minimise the flow distances.

The angle of the inner wall 65 can also be considered.

Holes can be fabricated with the angle of the walls 65 of the hole at any required value. Punching produces walls which are nominally orthogonal to the faces of the carrier 56 and this is preferred in most cases.

However, holes which are slightly larger at the face out of which the insert will be pushed provide less resistance whilst retaining the ability to guide the motion of the insert.

This may be required for some embodiments.

Where required, such holes can be machined or, with the appropriate conditions and materials, a sufficient angle may be achievable even with a punching manufacturing method.

The preferred wall angle for the current embodiment is between straight (90 degrees to the face) and 3 degrees from straight, more preferably 1 degree.

The insert moulding process requires the carrier plate to be placed inside a mould tool designed to restrict the plastic to the required insert form.

Where the carrier plate is made from an incompressible material and the mould tool closes on itself then, if the thickness of the carrier plate is less than the space allowed for it, there will be a gap into which the plastic may flow causing flashing.

Where the container is used for an inhalable material, any flashing could break free during use and be inhaled. This would not be acceptable.

To prevent this, the tolerance on the thickness of the carrier plate must be tight enough never to allow a gap into which plastic would flow during the moulding.

Preferably, this is less than 0.1 mm, more preferably 0.05 mm or less, where such tolerance control is not achievable, the mould tool could be designed to form a seal against the carrier plate surface rather than against another part of the mould tool.

Whilst the method of manufacture as described above could be applied to holes of any shape, there are effects of the shape that can be considered in the overall design.

The insert moulding material fully fills the allowed volume during injection of the plastic material. However, as the material cools and solidifies, it may expand or contract. The amount of this change can be controlled by the material and process conditions.

If there is too much shrinkage, then the inserts may be loose and may fall out. Also, gaps may be formed between the insert wall and the hole wall and the contained material, such as powder, may enter these gaps.

If there is too much expansion, then any straight sided walls will bow inwards, reducing the volume of the pocket. Similarly, the insert may stick in place.

Walls that have a convex shape will be more tolerant of any expansion, because they will not buckle inwards under low levels of compression. This is in contrast to straight or concave walls.

However, for the embodiment shown in FIG. 9, the pocket shape and anvil 62 are designed to rupture the foil around three sides causing a flap of foil 61 to pivot upwards on the fourth side. This is achieved by allowing a gap between the anvil edge and the edge of the pocket on the fourth side where the foil will pivot.

This operation, however, is made more reliable if the pivoting side is substantially straight. Thus, for this embodiment, the material and process for forming the pockets is preferably chosen to avoid any substantial expansion on cooling.

In the preferred manufacturing process, the carrier plate is placed in a mould tool so that part of the mould tool wall is located in the centre of the hole with a gap around it that is filled with plastic to form the insert. However, if the protrusion is not exactly centred on the hole then one wall will be thicker than its opposing wall. At some point, the thickness of the thin wall will not meet its mechanical strength requirements or even may not be sufficiently thick to allow it to fill fully with plastic during the moulding process.

There is therefore a tolerance requirement for the size and position of the hole with respect to the protuberance in the mould tool.

It has been recognized that it becomes difficult to mould walls thinner than 0.2 mm. Thus for a wall thickness of 0.3 mm the positional tolerance should be ±0.1 mm.

Specific tolerances for particular embodiments can be determined by the overall mechanical requirements.

Where single holes are being insert moulded, the tolerance requirements can easily be achieved. However, where an array of holes on a common carrier plate are to be moulded in one shot, the achievement of that tolerance may be more difficult. For example, a square array with a 100 mm side length and with square inserts with 0.3 mm walls preferably has a positioned alignment of ±0.05 mm and an angular alignment of 2 arc-minutes (0.03 degrees).

The alignment requirements can be reduced by careful design of the array. For example, a circular array of 100 mm diameter with inserts that are longer in the radial direction than in the circumferential direction is much less sensitive to angular misalignment than a square array. Furthermore, it is mechanically easier to centre mould tools for two circular arrays than it is for square ones.

The adhesion of the insert 20 in the through hole 18 will additionally depend on a number of parameters including the pre heat temperature of the carrier 10 and the materials chosen for the insert 20 and carrier 10 as well as the parameters affecting the fit described above. The insert 20 is preferably made from thermoplastic or thermosetting polymer, resin or any material that can be injected as a fluid and then converted to a solid when in situ, for instance a polymer, elastomer or monomer.

Where the carrier plate is made of a metal it will not be effected by the insert moulding process.

However carrier plates of plastic may also be used. In this case, it is necessary to consider the interactions that can occur during the insert moulding process.

If the melting point of the carrier plate material is much higher than the temperature of the insert plastic when it is injected then there will be little interaction.

However, where the carrier plate melting point is similar or lower than that of the insert material, the process must be controlled to minimise melting of the carrier plate material around the pocket.

When a sealing foil is to be welded to the carrier plate, this requires melting of the surface in contact with the foil. There is then a requirement to use a carrier plate material with a lower melting point than that of the insert material so as to avoid damaging the insert during the sealing process.

Counter-intuitively, it has been found possible to successfully mould polypropylene inserts into a polyethylene carrier plate even though the melting point of polypropylene is much higher than polyethylene.

This is achieved by optimising the time, pressure and temperature of the process for the particular geometry and materials being used. For the materials referred to above with inserts with walls 0.3 mm thick in a 3 mm thick carrier plate, the moulding parameters below were found to be preferred:

| | |
|---|---|
| Pressure - | 100 bar |
| Temperature - | 215 degrees Celsius |
| Time - | 2 seconds |

However, with these conditions, a small amount of melting of the carrier plate could occur and which could lead to adhesion between the inserts and the carrier plate. It has been found that this bond could be broken without damage to either component but this requires a higher force than is desirable for routine operation. To overcome this, each insert can be pressed partially out of its hole so as to break the bond. It can then be reset to its original location. Subsequently, it can be moved with a much lower force.

Typically, the force needed to initially release an insert of area 20 mm$^2$ in a 3 mm thick carrier plate of HDPE is between 50N and 100N. Following the initial bond breaking, the force required can be less than 30N.

Careful selection of gating technique will help to avoid gating marks on the insert 20 as well as separating the moulding sprue from the components.

The plastic flows into the mould during insert moulding through one or more channels in the walls of the mould tool. When the mould is full, one or more gates close off the plastic in the mould from the still molten plastic in the feed channels.

It is difficult to make the surface of the insert smooth at the gate location and flashing or pips may occur. In the preferred embodiment, the gate area is on the bottom of the insert over which foil will be applied to seal the compartment.

Flashing or sharp pips extending beyond the surface may risk puncturing of the foil.

A gating arrangement to prevent this is therefore preferred. An example of this is shown in FIG. 10.

FIG. 10(a) shows the flashing that can occur when the gate is located at the surface of the component.

FIG. 10(b) shows a variation where the gate is positioned slightly below the surface so that a hollow is formed within which the flashing can be recessed. This may be sufficient. However, there is still a chance that some sharp edge will still be above the surface.

FIG. 10(c) shows the situation where the protruding material has been flattened and deformed into the recess. This may be achieved by heat, ultrasonic or other means of locally melting the plastic and pushing it below the surface using a hard flat tool.

In this way it can be ensured that no sharp edges will be above the surface to damage the foil.

Thus, it is possible to produce an insert 20 in each through hole 18 with a required shape such that the insert 20 is a close fit to the walls 16 of the carrier 10. This prevents the medicament penetrating past the insert 20, but allows the insert to move freely when pushed from below. The technique is generally suitable for the manufacture of assemblies which contain a multiple of components with sliding or rotating fits which would otherwise have to be individually assembled. It thus represents a saving in materials handling and assembly costs.

When the carrier 10 is removed from the mould 40,42, it contains the insert 20. In accordance with the parameters discussed above, in the preferred embodiment, the insert 20 is held resiliently in place within the carrier 10. In this way, no additional process steps are required to maintain the insert 20 in position.

The insert or inserts of the carrier 10 may then be filled with medicament. The medicament may be provided in any suitable form, for instance as a tablet, powder or liquid. However, the container constructed as described is particularly advantageous for use with dry powder.

The medicament may be dispensed into the insert cavities 24 of the inserts 20 from a device which dispenses doses of a predetermined quantity. However, as mentioned above, the insert cavity 24 can be chosen with a predetermined volume such that filling the insert cavities 24 results in the container housing the required doses of medicament.

The lidding sheets 12 and 14 may then be fixed to the first and second faces of the carrier 10 so as to seal the inserts 20 and medicament within the through holes 18. Preferably, the sheets are hermetically sealed. This is particularly advantageous for dry powders. The lidding sheet may be constructed of aluminium foil, although any other suitable material which provides the required barrier properties may be used.

It is also possible for the second sheet to be sealed to the second face before the step of filling with medicament.

Furthermore, as an alternative to the method discussed above, the cup-shaped space may be filled with moulding material from the first face, for instance via a filling channel in the projecting element. In this case, it is possible to seal the second sheet to the second face before or during the moulding step. If the second sheet is placed between the lower mould and the carrier 10, then it is possible to seal it to the carrier at the same time as filling the cup-shaped space with moulding material, for instance by heating.

The invention claimed is:

1. A method of manufacturing a container for housing at least one individual dose of medicament using a carrier having first and second opposing faces and through walls defining a through hole extending between the first and second opposing faces, the method including:
   inserting the carrier into a mould having an element for protrusion into the through hole from the first face so as to define with the through walls a generally cup-shaped space;
   filling the generally cup-shaped space with a moulding material so as to form a generally cup-shaped insert in the through hole; and
   removing the carrier and insert from the mould whereby an individual dose of medicament may be deposited in the generally cup-shaped insert and the medicament and insert sealed in the through hole by means of first and second sheets sealed respectively with the first and second faces.

2. A method of manufacturing a container housing at least one individual dose of medicament using a carrier having first and second opposing faces and through walls defining a through hole extending between the first and second opposing faces, the method including:
   inserting the carrier into a mould having an element for protrusion into the through hole from the first face so as to define with the through walls a generally cup-shaped space;
   filling the generally cup-shaped space with a moulding material so as to form a generally cup-shaped insert in the through hole;
   removing the carrier and insert from the mould;
   depositing an individual dose of medicament in the generally cup-shaped insert; and
   sealing the medicament and insert in the through hole by sealing first and second sheets respectively with the first and second faces.

3. A method according to claim 1 further including:
   forming said carrier with said through hole.

4. A method according to claim 3 further including:
   forming said carrier by one of injection moulding, die casting, pressing, extrusion, casting, sintering, stamping, punching and coining.

5. A method according to claim 3 further including:
   forming said carrier from one of polymers, metals, ceramics and composites.

6. A method according to claim 3 further including:
   forming said carrier from a moisture impermeable material such as a low permeability plastic, composite or aluminium.

7. A method according to claim 1 further including:
   forming said insert from one of a polymer, elastomer and monomer.

8. A method according to claim 1 further including:
   forming said first and second sheets from aluminium or any low permeability sheet material such as Aclar, CTE or Barrex.

9. A method according to claim 1 wherein the fit of the insert in the through hole is controlled by controlling at least one of the injection pressure, the injection temperature, the surface finish of the through walls and a draught angle of the through walls.

10. A method according to claim 1 wherein the sealing of the insert in the through hole is controlled by controlling at least one of the preheat temperature of the carrier, the material of the insert and the fit of the insert.

11. A method according to claim 1 wherein the mould at the second face is generally flush and co-planar with the second face.

12. A method according to claim 2 wherein the generally cup-shaped space is filled with the moulding material from the second face.

13. A method according to claim 1 wherein the second sheet is sealed to the second face before or during the step of filling the cup-shaped space with moulding material.

14. A method of manufacturing according to claim 1 further including
   varying the size of the element so as to vary the volume of the cup-shaped space between different containers.

* * * * *

UNITED STATES PATENT AND TRADEMARK OFFICE
CERTIFICATE OF CORRECTION

| | |
|---|---|
| PATENT NO. | : 7,588,030 B2 |
| APPLICATION NO. | : 10/503818 |
| DATED | : September 15, 2009 |
| INVENTOR(S) | : Ede et al. |

It is certified that error appears in the above-identified patent and that said Letters Patent is hereby corrected as shown below:

On the Title page,

[*] Notice:    Subject to any disclaimer, the term of this patent is extended or adjusted under 35 USC 154(b) by 1209 days Delete the phrase "by 1209 days" and insert -- by 1440 days --

Signed and Sealed this

Twentieth Day of April, 2010

David J. Kappos
*Director of the United States Patent and Trademark Office*